US010716861B2

(12) United States Patent
Robic et al.

(10) Patent No.: US 10,716,861 B2
(45) Date of Patent: Jul. 21, 2020

(54) COMPOSITION INTENDED TO VECTORISE AN ANTI-CANCER AGENT

(71) Applicant: GUERBET, Villepinte (FR)

(72) Inventors: Caroline Robic, Nogent sur Marne (FR); Jean-François Mayer, Aulnay sous Bois (FR)

(73) Assignee: GUERBET, Villepinte (FR)

( * ) Notice: Subject to any disclaimer, the term of this patent is extended or adjusted under 35 U.S.C. 154(b) by 14 days.

(21) Appl. No.: 15/750,282

(22) PCT Filed: Aug. 4, 2016

(86) PCT No.: PCT/EP2016/068687
§ 371 (c)(1),
(2) Date: Feb. 5, 2018

(87) PCT Pub. No.: WO2017/021508
PCT Pub. Date: Feb. 9, 2017

(65) Prior Publication Data
US 2019/0099496 A1    Apr. 4, 2019

(30) Foreign Application Priority Data
Aug. 4, 2015 (FR) ...................................... 15 57524

(51) Int. Cl.
| | |
|---|---|
| *A61K 47/44* | (2017.01) |
| *A61K 9/00* | (2006.01) |
| *A61K 47/14* | (2017.01) |
| *A61K 9/107* | (2006.01) |
| *A61K 49/04* | (2006.01) |
| *A61K 49/08* | (2006.01) |
| *A61K 49/10* | (2006.01) |
| *A61K 47/02* | (2006.01) |
| *A61P 35/04* | (2006.01) |
| *A61K 45/06* | (2006.01) |

(52) U.S. Cl.
CPC ............ *A61K 47/44* (2013.01); *A61K 9/0019* (2013.01); *A61K 9/107* (2013.01); *A61K 45/06* (2013.01); *A61K 47/02* (2013.01); *A61K 47/14* (2013.01); *A61K 49/0461* (2013.01); *A61K 49/085* (2013.01); *A61K 49/106* (2013.01); *A61P 35/04* (2018.01); *A61K 49/101* (2013.01)

(58) Field of Classification Search
None
See application file for complete search history.

(56) References Cited

U.S. PATENT DOCUMENTS

| | | | |
|---|---|---|---|
| 4,404,182 A | 9/1983 | Vermess et al. | |
| 5,312,615 A | 5/1994 | Schneider et al. | |
| 5,468,467 A * | 11/1995 | Tweedle .................. | A61K 49/06 424/9.361 |
| 2001/0036451 A1 | 11/2001 | Goupil et al. | |
| 2004/0029977 A1 | 2/2004 | Kawa et al. | |
| 2004/0241094 A1 | 12/2004 | Chung et al. | |

(Continued)

FOREIGN PATENT DOCUMENTS

| | | |
|---|---|---|
| DE | 2602907 B1 | 7/1977 |
| EP | 0294534 A1 | 12/1988 |

(Continued)

OTHER PUBLICATIONS

Wolf et al., "Stabilization of water Droplets in Oil with PGPR for Use in Oral and Dermal Applications", Journal of Food Process Engineering, 2012, p. 276.

(Continued)

*Primary Examiner* — James W Rogers
(74) *Attorney, Agent, or Firm* — Thompson Coburn LLP; Steven M. Ritchey

(57) ABSTRACT

A composition in the form of a water-in-oil emulsion comprising:
  from 20% to 40% (v/v) of aqueous phase, in the form of droplets, comprising an anti-cancer agent and a densifying agent chosen from the complexes of nonionic macrocyclic chelate with a paramagnetic metal,
  from 60% to 80% (v/v) of lipid phase comprising an iodized oil and at least one surfactant of formula (I) in a proportion, by weight of surfactant relative to the total volume of the composition, of 0.3% to 5%, formula (I) of said surfactant being the following:

$$R_2 \!-\!\!\left[\!O\!-\!\!\left[\phantom{x}\right]_s\!\right]_m\!\!O\!-\!R_1 \quad (I)$$
$$\phantom{xxxxxxxxx}OR_3$$

in which:
s is 0 or 1,
m is an integer from 2 to 30,
$R_1$ represents a group of formula (II)

$$\text{(II)}$$

in which n is an integer from 4 to 10, o is an integer from 1 to 4, p is an integer from 3 to 7, q is an integer from 2 to 10, and r is 0 or 1,
$R_2$ represents a hydrogen atom or is identical to $R_1$, and each $R_3$ independently represents a hydrogen atom or is identical to $R_1$.

13 Claims, No Drawings

(56) References Cited

U.S. PATENT DOCUMENTS

| | | |
|---|---|---|
| 2008/0044543 A1 | 2/2008 | McClements et al. |
| 2010/0233221 A1 | 9/2010 | Folmer et al. |

FOREIGN PATENT DOCUMENTS

| | | |
|---|---|---|
| EP | 0581842 B1 | 6/1999 |
| EP | 0740581 B1 | 11/2004 |
| EP | 2077106 A1 | 7/2009 |
| EP | 1931673 B1 | 8/2012 |
| EP | 2719398 A2 | 4/2014 |
| JP | H0647559 B2 | 6/1994 |
| JP | H10-158152 A | 6/1998 |
| JP | 2005068058 A | 3/2005 |
| JP | 2005506274 A | 3/2005 |
| JP | 2010514560 A | 5/2010 |
| WO | 03022264 A1 | 3/2003 |
| WO | 2007071261 A2 | 6/2007 |
| WO | 2008083092 A2 | 7/2008 |
| WO | 2012/173003 A2 | 12/2012 |
| WO | 2014174120 A1 | 10/2014 |
| WO | 2015-118113 A1 | 8/2015 |

OTHER PUBLICATIONS

De Baere et al., "Circulatory Alterations Induced by Intra-Arterial Injection of Iodized Oil and Emulsions of Iodized Oil and Doxorubicin: Experimental Study", Radiology, Jan. 1995, pp. 165-170, vol. 194, No. 1.

Higashi et al., "Hepatic Arterial Injection Chemotherapy for Hepatocell,ular Carcinoma with Epirubicin Aqueous Solution as Numberous Vesicles in Iodinated Poppy-Seed Oil Microdroplets: Clinical Application of Water-In-Oil-In-Water Emulsion Prepared Using a Membrane Emulsification Technique", Advanced Drug Delivery Reviews, 2000, pp. 57-64, vol. 45.

Hong et al., "New Intra-Arterial Drug Delivery System for the Treatment of Liver Cancer: Preclinical Assessment in a Rabbit Model of Liver Cancer", Clinical Cancer Research, Apr. 15, 2006, pp. 2563-2567, vol. 12, No. 8.

Idée et al., "Use of Lipiodol as a Drug-Delivery System for Transcatheter Arterial Chemoembolization of Hepatocellular Carcinoma: A Review", Critical Reviews in Oncology/Hematology, Dec. 2013, pp. 530-549, vol. 88 Issue 3.

International Search Report and Written Opinion for PCT/EP2016/068687 dated Oct. 14, 2016.

Nakamura et al., "Transcatheter Oily Chemoembolization of Hepatocellular Carcinoma", Radioloy, Mar. 1989, pp. 783-786, vol. 170.

Raoul et al., "Chemoembolization of Hepatocellular Carcinomas. A Study of Biodistribution and Pharma-Cokinetics of Doxorubicin", Cancer Aug. 1, 1992, pp. 585-590, vol. 70, No. 3.

Schumacher et al., "Experimental Data on the Problem of Specific Hepatosplenography with Radiodense Lipomicrons", European Journal of Radiology, 1985, pp. 167-174, vol. 5.

Shiono et al., "Efficacy of Emulsion Containing Gd-DTPA and Lipiodol in Hepatic Transcatheter Arterial Embolization", Radiation Medicine, Sep. 1993, pp. 187-190, vol. 11, No. 5.

Vermess et al., "Development and Experimental Evaluation of a Contrast Medium for Computed Tomographic Examination of the Liver and Spleen", Journal of Computer Assisted Tomography, Feb. 1979, pp. 25-31, vol. 3, No. 1.

Yi et al., "Stable Lipiodolized Emulsions for Hepatoma Targeting and Treatment by Transcatheter Arterial Chemoembolization", Journal of Controlled Release, Jan. 2, 1998, pp. 135-143, vol. 50, No. 1-3.

Ankoh, "Lecithin Lipiodol Emulsion: Experimental Study on Transcatheter Hepatic Arterial Chemoembolization Using Lecithin-Containing Lipiodol Emulsion", Journal of Tokyo Women's Medical College, Jan. 1, 1990, pp. 999-1010, vol. 60, No. 12.

\* cited by examiner

COMPOSITION INTENDED TO VECTORISE AN ANTI-CANCER AGENT

CROSS-REFERENCE TO RELATED APPLICATIONS

This application is a U.S. National Phase application of PCT/EP2016/068687, filed on Aug. 4, 2016, claiming the benefit of French Application No. 1557524, filed on Aug. 4, 2015, each of which is incorporated herein by reference in its entirety.

The present invention relates to a composition in the form of a water-in-oil emulsion comprising an anti-cancer agent, a densifying agent chosen from the complexes of nonionic macrocyclic chelate with a paramagnetic metal, an iodized oil and a surfactant.

For more than a century, iodized oils such as the product Lipiodol® have been used as contrast products in radiological examinations such as lymphography or for the diagnosis of hepatic lesions. Lipiodol® consists mainly of ethyl esters of iodized fatty acids of poppy oil.

For more than thirty years, these iodized oils have been used in interventional radiology procedures. Lipiodol® is characterized by its propensity to be selectively taken up by hepatic tumors. It has therefore been proposed as an anti-cancer agent vector for the treatment of hepatocellular carcinoma in a technique which is called TransArterial ChemoEmbolization (TACE) (Nakamura et al.: Radiology, 1989; 170:783-6 and J. M. Idée-B. Guiu: Critical Reviews in Oncology/Hematology, 2013; 88(3):530-49). Iodized oils, and in particular Lipiodol®, are also known to induce transient embolization of the arterial circulation, thus causing a slowing down thereof. Given that most anti-cancer agents are water-soluble, the "emulsion" form, which is suitable for mixing two phases not soluble in one another, appears to be the most judicious for mixing an iodized oil and an anti-cancer agent. It appears to be the most suitable for transporting and delivering, to a tumor, an anti-cancer agent which is too toxic and not effective enough when it is administered non-emulsified intra-arterially or systemically.

A "water-in-oil" emulsion, termed "inverse" emulsion, is an emulsion which is denoted W/O (water-in-oil). It is a dispersion of droplets of aqueous phase in a lipid phase. An "oil-in-water" emulsion is a "direct" emulsion that is denoted O/W (oil-in-water). Unlike W/O emulsions, it is then a dispersion of droplets of lipid phase in an aqueous phase. The term "sense of the emulsion" is used when referring to the W/O or O/W nature of an emulsion.

Oil-in-water (O/W) emulsions, which comprise the anti-cancer agent in the aqueous continuous phase, have the considerable drawback of rapidly releasing the anti-cancer agent in the blood. A not insignificant part of the therapeutic agent does not therefore reach the targeted site, which may, on the one hand, induce systematic toxicity and, on the other hand, reduce the efficacy of this therapeutic agent. Furthermore, this type of O/W emulsion has the risk of causing a pulmonary or even cerebral embolism. This risk is increased when the size of the droplets of oil of these emulsions is less than 10 μm. This second drawback is difficult to exclude since, when increasing the size of the droplets, the instability of these emulsions is increased.

Water-in-oil (W/O) emulsions, also called "inverse emulsions", and comprising an iodized oil and an anti-cancer agent, are less commonly mentioned in the literature than O/W emulsions. They are described as releasing the therapeutic more slowly in the tumor and as having a higher viscosity than oil-in-water emulsions (De Baere et al., Radiology 1995; 194:165-170). These reasons lead to the choice of a form of W/O emulsion for vectorizing an anti-cancer agent within a tumor. However, these W/O emulsions are not always sufficiently effective because of their lack of stability on contact with the blood and the vascular bifurcations upstream of the tumor. Indeed, in order to increase the tumor targeting of anti-cancer agents and to at the same time improve the therapeutic efficacy and the tolerance of the treatment, an emulsion must remain stable up to the moment it reaches the tumor, and its distribution in the tumor lesion must be complete and uniform.

Various solutions for stabilizing emulsions have thus been proposed in the prior art. Numerous authors have proposed the use of surfactant with a high HLB (more than 8) for stabilizing O/W emulsions.

The use of surfactant with a high or even very high HLB, such as the polyoxyethylenated fatty acid esters of sorbitan, polyoxyethylenated sorbitan monostearate or polysorbate 60 (Montanox® 60, HLB=14.9) and polyoxyethylenated sorbitan monolaurate or polysorbate 20 (Montanox 20®, HLB=16.7), has been described for preparing oil-in-water emulsions based on idarubicin and Lipiodol®, which are stable for 6 months.

JPH0647559 describes an O/W emulsion comprising between 10% and 30% of Lipiodol®, an anti-cancer agent and between 0.1% and 2% of a hydrophilic surfactant, HCO-60, otherwise known as polyoxyethylene hydrogenated castor oil (HLB=14). It is, a priori, a PEG-60 bonded to a ricinoleic acid.

Applications EP 0 294 534 and EP 0 581 842 refer to other documents. It is in particular discovered that DE 26 02 907 describes an oil-in-water emulsion containing between 50% and 60% of iodized triglycerides, between 2% and 10% of fatty acid esters of polyoxyethylene sorbitan (HLB=13 to 17) and between 2% and 40% of water. Grimes et al. (J. Pharm. Sci. 1979 January; 68(1):52-6) describes the use of polysorbate 80 (HLB=15), of sorbitan monooleate (HLB=8.6) and of phosphatidylcholine for obtaining emulsions comprising iodized oil. Vermess et al. has described emulsions (U.S. Pat. No. 4,404,182 or J. Comput. Assist. Tomogr. 3: 25-31, 1979) containing 53% (v/v) of Lipiodol®, 10% of alcohol and 0.45% of soya lecithin. These oil-in-water emulsions have particles sizes of 2 to 5 μm. Schumacher et al. (Europ. J. Radiol. 5, 167-174, 1985) describes various emulsions containing iodized oils prepared using emulsifiers such as polyoxyethylene-4-sorbitan monolaurate (Tween® 80, Serva: HLB=15.3), glycerol polyethylene glycol ricinoleate (Cremophor® EL: HLB=14.5), diacetylphosphate DP (Sigma), lecithin from eggs (Fluka GmbH), doxypolygelatin (Gelinfundol® 5.5% Biotest GmbH) and dextran 60 (Macrodex®4.5%, RL Knoll).

The use of amiodarone (an antiarythmic medicament of chemical formula (2-butyl-3-benzofuranyl)[4-[2-(diethylamino)ethoxy]-3,5-diiodophenyl]methanone) has made it possible to stabilize an oil-in-water emulsion of Lipiodol® (44% (v/v)) and doxorubicin or pirarubicin, for up to four weeks at 37° C. This property is due to the presence, in this medicament, of an excipient, polysorbate 80, which is an emulsifier with a high HLB (Boulin et al., Digestive and Liver Disease 43 (2011) 905-911). Additional studies by the same team have made it possible to show that amiodarone provides virtually no improvement in the stability of an emulsion based on Lipiodol® and idarubicin, and does not appear to increase the cytotoxicity in the anti-cancer agent. The use alone of idarubicin and of Lipiodol® is therefore even recommended.

Nakamura et al. (Radiology, 1989; 170:783-6) shows the visual appearance of various emulsions obtained by mixing 1 ml of distilled water comprising an ionic contrast product, meglumine sodium diatrizoate (Hypaque®, Gastrografin® or Urografin®) and 3 ml of Lipiodol® (FIG. 1). It is indicated that the emulsion C did not undergo phase separation after 24 h, but it can be easily noted in this figure that this emulsion is in reality not stable, the lower part of the tube that contains it being clearer than the upper part thereof. This document also describes the preparation of an emulsion of Lipiodol® and of doxorubicin or mitomycin in ratios of 2-3/1. It is indicated that the emulsion obtained is a W/O emulsion. The lowest amount of release of anti-cancer agent in the case of the use of this emulsion is emphasized (FIG. 2). The plasma peak visualized after injection of this emulsions remains, however, not insignificant. This emulsion must not be sufficiently stable since there is no use of surfactant. Indeed, 2 minutes after intra-arterial injection of their emulsion, a plasma concentration of doxorubicin is observed which is 83% lower (((3500−600)/3500)×100) compared with the plasma concentration measured after injection of this anti-cancer agent alone. At 5 minutes, this decrease is 80%.

Raoul et al. (Cancer, 1992, vol. 70, No. 3, 585-90), describes emulsions comprising 50 mg of doxorubicin, made by mixing 10 ml of Lipiodol® and 2.5 ml of ioxaglate (Hexabrix®). The emulsions obtained, the W/O or O/W sense of which is not specified, cause a plasma peak that is significantly lower than that caused by the intra-arterial injection of doxorubicin alone. However, this plasma peak indicates a not insignificant passing of the anti-cancer agent into the blood. Indeed, 2 minutes after intra-arterial injection of these emulsions, a plasma concentration of doxorubicin is observed that is 59% lower (((2200−900)/2200)×100) compared with the plasma concentration measured after injection of this anti-cancer agent alone. The calculation corresponding to 5 minutes after injection is even more unfavorable since this decrease is then only 33% (((1050−700)/1050)×100). When an embolization is performed after injection of these emulsions, these decreases are, at 2 and 5 minutes, respectively 82% (((2200−400)/2200)×100) and 43% (((700−400)/700)×100).

These various emulsions, when they are in "oil-in-water" form, have an insufficient anti-cancer agent-vectorizing capacity, even if they have been stabilized using a surfactant with a high HLB, and their use still exhibits a significant risk of embolism. This insufficient vectorization capacity is explained by the very nature of the emulsion, since, in the case of oil-in-water emulsions, the anti-cancer agent, which is usually water-soluble, is in the aqueous continuous phase and is therefore very rapidly diluted in the blood stream. In addition, several of these emulsions contain synthetic emulsifiers such as Tweens® (high HLB) or Spans® (either lower or higher HLB), which are emulsifiers listed in the European pharmacopoeia, and which cause side effects. Polysorbates such as Tweens® are described as potentially toxic. Sorbitan esters such as Spans® are not recommended for use by parenteral injection (Handbook of Pharmaceutical Excipients, 2009).

Frequently, emulsions described in publications as "water-in-oil" emulsions are not emulsions of this nature. This is the case for example with the emulsions described in the publication by Yi et al. (Journal of Controlled Release 50 (1998) 135-143) or with the intermediate emulsion described in Higashi et al. (Advances Drug delivery Reviews 45 (2000), 57-64). When they are actually in the W/O form, these emulsions have insufficient stabilities and insufficient anti-cancer agent-vectorizing capacities. They therefore have an insufficient efficacy after injection since a considerable part of the amount of anti-cancer agent injected intra-arterially does not reach the targeted lesion (Raoul et al., 1992).

To prepare the majority of the emulsions described in the prior art, iodinated contrast products, such as a densifying agent, preferentially nonionic iodinated contrast products, are used. These contrast products, which are present in the same phase as the anti-cancer agent (i.e. the aqueous phase), can be visualized by X-ray imaging techniques. However, the iodized oil present in the oily phase can also be visualized by this imaging mode. Having an increase in the contrast both in the aqueous phase and in the oily phase prevents the verification, using an imaging technique, of the colocalization of the anti-cancer agent and of the densifying agent.

The applicant has developed a composition which makes it possible to prepare a water-in-oil emulsion comprising an anti-cancer agent which is stable for at least 24 h at 20° C. and which generally has an improved vectorizing capacity compared with the prior art emulsions, while allowing a more precise double control of its efficacy by a magnetic resonance imaging (MRI) technique and by an X-ray imaging technique.

This emulsion therefore has three major advantages: it can be easily used in a hospital context, since its stability allows it to be prepared at least 24 hours in advance in the hospital pharmacy, it presents a very limited risk to the patient, while at the same time having an improved therapeutic efficacy and its efficacy can be more easily measured by an imaging technique than the efficacy of the conventional emulsions of the prior art.

This emulsion also has the advantage of making it possible to correlate an amount of iodized oil (e.g. Lipiodol®) present in a tumor, which may be estimated by means of an X-ray imaging method, with an amount of anti-cancer agent actually present in the tumor. For the majority of prior art emulsions, the amount of iodized oil that is estimated to be present in a tumor is in no way an indication of the amount of anti-cancer agent present in this tumor. The emulsion according to the invention therefore makes it possible to reduce the false positives when seeking to verify that the anti-cancer agent has effectively been administered at the heart of the tumor and it also makes it possible to obtain a better verification of the efficacy thereof by means of another imaging mode, such as magnetic resonance imaging.

Thus, a subject of the invention is a composition in the form of a water-in-oil emulsion comprising:

from 20% to 40% (v/v) of aqueous phase, preferentially from 20% to 35% (v/v), more preferentially 25% (v/v), of aqueous phase, in the form of droplets, comprising an anti-cancer agent and a densifying agent chosen from the complexes of nonionic macrocyclic chelate with a paramagnetic metal, preferentially with a lanthanide, more preferentially with gadolinium, from 60% to 80%, preferentially from 65% to 80% (v/v), more preferentially 75% (v/v), of lipid phase comprising an iodized oil and at least one surfactant of formula (I) in a proportion, by weight of surfactant relative to the total volume of the composition, of 0.3% to 5%, preferentially of 0.5% to 2%, more preferentially of 1%, formula (I) of said surfactant being the following:

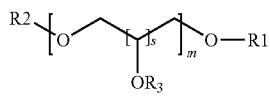
(I)

in which:
s is 0 or 1,
m represents an integer from 2 to 30,
$R_1$ represents a group of formula (II)

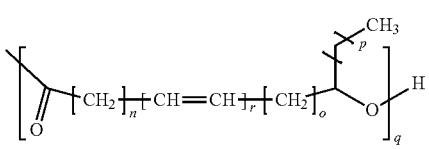
(II)

in which n represents an integer from 4 to 10, o represents an integer from 1 to 4, p represents an integer from 3 to 7, q represents an integer from 2 to 10 and r is 0 or 1,
$R_2$ represents a hydrogen atom or is identical to $R_1$, and each $R_3$ independently represents a hydrogen atom or is identical to $R_1$.

Preferably, in formula (I) above, each $R_3$ represents a hydrogen atom. Formula (I) of said surfactant then has the following formula (I'):

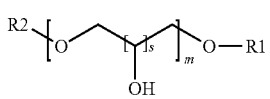
(I')

The proportion of surfactant is expressed by weight of surfactant relative to the total volume of the composition in emulsion form. The proportions of aqueous or lipid phases are expressed by volume of the phase relative to the total volume of the composition in emulsion form.

This composition is for vectorizing an anti-cancer agent. The invention also relates to the use of this composition as an anti-cancer agent vector.

This composition is in the form of a water-in-oil emulsion (also known as "inverse emulsion" or W/O emulsion). Such an emulsion consists of a lipid phase and an aqueous phase dispersed in the form of droplets. The iodized oil of the composition is in the lipid phase. The surfactant of formula (I) or (I') is at the interface between the aqueous and lipid phases. For the purposes of the present application, for the calculation of the proportions of aqueous and lipid phases, it will be considered that the surfactant is in the lipid phase.

In particular, the following embodiments are advantageous:

| | % (v/v) of aqueous phase in the form of droplets comprising an anti-cancer agent | % (v/v) of lipid phase comprising an iodized oil | % (w/v) of at least one surfactant |
|---|---|---|---|
| Composition in emulsion form according to the invention | 20-35 | 65-80 | 0.5-2 |

| | % (v/v) of aqueous phase in the form of droplets comprising an anti-cancer agent | % (v/v) of lipid phase comprising an iodized oil | % (w/v) of at least one surfactant |
|---|---|---|---|
| Composition in emulsion form according to the invention | 25 | 75 | 1 |

The emulsion according to the invention is advantageously stable. The term "stable emulsion" is intended to mean an emulsion having, under conventional temperature (20° C.) and atmospheric pressure (1 bar) conditions and within 24 hours following its preparation, a visual phase separation of less than 5% by volume relative to the total composition in emulsion form. Preferentially, a "stable emulsion" is intended to mean an emulsion exhibiting no visual phase separation under the conditions mentioned above and within 24 hours following its preparation. Visual phase separation manifests itself when a solution no longer appears uniform to the eye, i.e. when the appearance of at least two phases is observed.

More preferentially, the term "stable emulsion" is intended to mean an emulsion of which the average droplet size varies by less than 10%, in particular by less than 5%, preferably of which the average droplet size does not vary, wherein the average size is measured with an optical microscope (for example the Leica DM2000 LED microscope) 24 hours after its preparation.

Preferably, the intra-arterial injection of the emulsion according to the invention induces a decrease in the plasma concentration of the anti-cancer agent between 0 and 5 minutes following this injection of more than 90%, preferentially of more than 94%, more preferentially of more than 97%, even more preferentially of more than 99%, relative to the intra-arterial injection of the anti-cancer agent alone. Advantageously, these plasma concentrations and this decrease are confirmed by plasma kinetics measurements according to protocols known to those skilled in the art.

The expression of the difference between a plasma concentration peak of an anti-cancer agent after injection of a particular product comprising this agent and that obtained after injection of the anti-cancer agent alone is in particular mentioned by Hong et al. (Clin. Cancer Res. 2006: 12(8)).

When the emulsion comprises less than 20% (v/v) of aqueous phase, the anti-cancer agent is difficult to dissolve therein. When the emulsion comprises more than 40% of aqueous phase, the viscosity of the composition in emulsion form is too high. This is because, when increasing the concentration of droplets of aqueous phase in the lipid continuous phase comprising an iodized oil, the viscosity of the overall composition is increased.

The aqueous phase comprises an anti-cancer agent at a therapeutically effective dose. The term "therapeutically effective dose" is intended to mean a dose which makes it possible to treat a cancer or to slow down the progression thereof. Preferentially, when the anti-cancer agent is chosen from anthracyclines, a therapeutically effective dose represents an amount of anti-cancer agent of from 20 to 150 mg, more preferentially from 50 to 100 mg.

The density of the lipid phase is preferentially from 1.15 to 1.30, more preferentially from 1.20 to 1.30, even more preferentially 1.28. Preferentially, the aqueous phase and the lipid phase have the same density (in other words, they are of equal density) or densities up to 5% different than one another.

The densifying agent makes it possible to carry out a densification of the aqueous phase comprising an anti-cancer agent. In order to decrease the density of the lipid phase comprising an iodized oil, a second oil having a density of less than 1 can be added (a "dedensification" of the lipid phase comprising an iodized oil is then carried out).

Complexes of Nonionic Macrocyclic Chelate with a Paramagnetic Metal

In one advantageous embodiment, the complexes of nonionic macrocyclic chelate with a paramagnetic metal are chosen from Gd-HP-DO3A (International Nonproprietary Name: gadoteridol, commercial name: ProHance®), Gd-BT-DO3A (INN: gadobutrol, commercial name: Gadovist®), a complex of the formula (XI):

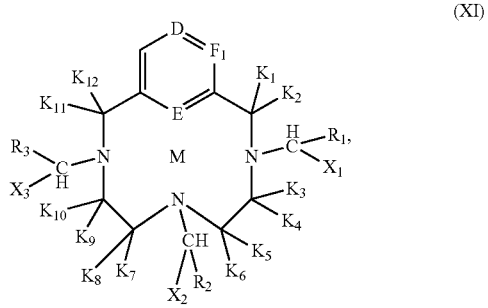

(XI)

in which $R_1$, $R_2$ and $R_3$ represent —COOH, $X_1$, $X_2$ and $X_3$ represent, independently of one another, L-Y in which L represents a $C_1$-$C_3$ alkylene group, preferably a $(CH_2)_n$ group with n=1 to 3, Y represents —CONH$_2$, —CO—NR$_7$R$_8$ or —NR$_7$—CO—R$_8$, in which $R_7$ represents H or a $C_1$-$C_6$ alkyl group or a $C_1$-$C_8$, in particular $C_2$-$C_6$, for example $C_2$-$C_4$, hydroxyalkyl group, advantageously —CH$_2$—CH$_2$OH, —CHOH—CH$_2$OH, —CH—(CH$_2$OH)$_2$, —(CH$_2$)$_m$—(CHOH)$_p$—CH$_2$OH with m=1 to 3 and p=1 to 4 or —C—(CH$_2$OH)$_3$ and $R_8$ represents a $C_1$-$C_6$ alkyl or $C_1$-$C_8$, in particular $C_2$-$C_6$, for example $C_2$-$C_4$, hydroxyalkyl group, advantageously —CH$_2$—CH$_2$OH, —CHOH—CH$_2$OH, —CH—(CH$_2$OH)$_2$, —(CH$_2$)$_m$—(CHOH)$_p$—CH$_2$OH with m=1 to 3 and p=1 to 4 or —C—(CH$_2$OH)$_3$, on the condition that at least $R_7$ or $R_8$ represents a $C_1$-$C_8$ hydroxyalkyl group;

D represents CH or N;
E represents CH or N;
$F_1$ represents CH or N;
$K_1$ to $K_{12}$ each independently represent H, —(CH$_2$)$_j$—CH$_3$ or —(CH$_2$)$_i$—OH in which j=0 to 3 and i=1 to 3, advantageously H, or $K_3$ or $K_4$ with $K_5$ or $K_6$, and/or $K_7$ or $K_8$ with $K_9$ or $K_{10}$ form, with the carbon atoms to which they are bonded, a ring having 3 to 6 carbon atoms; and M represents an ion of a paramagnetic metal;

or an enantiomer, or a diastereoisomer (preferentially chosen from the RRS, RSR, RSS diastereoisomers) thereof or mixtures thereof, and a mixture thereof.

When $R_7$ and/or $R_8$ represent —(CH$_2$)$_m$—(CHOH)$_p$—CH$_2$OH with m=1 to 3, p=1 to 4, each of the combinations between m=1, 2, 3 and p=1, 2, 3, 4, in particular m=2 and p=4, m=3 and p=4, or m=3 and p=3, is possible.

Preferably, when $R_7$ and/or $R_8$ represent a hydroxyalkyl group, they represent a $C_1$-$C_6$ hydroxyalkyl, advantageously —CH$_2$—CH$_2$OH, —CHOH—CH$_2$OH, —CH—(CH$_2$OH)$_2$, —(CH$_2$)$_m$—(CHOH)$_p$—CH$_2$OH with m=1 to 3, p=1 to 4 and m+p=2 to 5 or —C—(CH$_2$OH)$_3$.

Preferentially, the complexes of nonionic macrocyclic chelate with a paramagnetic metal have a density of 1.10 to 1.30, more preferentially of 1.20 to 1.30, even more preferentially of 1.28.

In one particular embodiment, the density of the nonionic macrocyclic chelate with a paramagnetic metal is increased up to a limiting maximum value of 1.30, either by evaporation if this compound is in liquid form, or by concentration if this compound is in powder form.

These complexes of nonionic macrocyclic chelate with a paramagnetic metal have the advantage of allowing good solubility of the anti-cancer agent in the aqueous phase and of not destabilizing the emulsion.

Complex of Formula (XI)

Particular preference is given to the complexes of formula (XI) for which the three Y chains each have a molecular weight of less than 200 g/mol, advantageously between 50 and 100 g/mol, and in particular the compounds for which the Y chains each comprise 1 to 5 OH groups.

According to advantageous implementations, the complex of formula (XI) is such that E represents an N and D atom and $F_1$ represents CH.

According to advantageous embodiments, the complex of formula (XI) is such that $X_1$, $X_2$ and $X_3$ independently represent —(CH$_2$)$_n$—CO—NR$_7$R$_8$ or —(CH$_2$)$_n$—NR$_7$—CO—R$_8$, in which n is between 1 and 3, $R_7$ represents H or a methyl group, $R_8$ represents a $C_1$-$C_6$, advantageously $C_2$-$C_3$, hydroxyalkyl group, preferably —CH$_2$—CH$_2$OH, —CHOH—CH$_2$OH, —CH—(CH$_2$OH)$_2$, —CH$_2$—(CHOH)$_p$—CH$_2$OH with p=1 to 4 or —C—(CH$_2$OH)$_3$. Advantageously, $X_1$ to $X_3$ independently represent —(CH$_2$)$_n$ CONR$_7$R$_8$ in which n is between 1 and 3, $R_7$ represents H or a methyl group, $R_8$ represents a $C_1$-$C_4$ hydroxyalkyl group, preferably —CH$_2$—CH$_2$OH, —CHOHCH$_2$OH, —CH—(CH$_2$OH)$_2$, —CH$_2$—(CHOH)$_p$—CH$_2$OH with p=1 or 2 or —C—(CH$_2$OH)$_3$. Advantageously, $X_1$ to $X_3$ independently represent —(CH$_2$)N—CONR$_7$R$_8$, in which n is between 1 and 3, $R_7$ represents H, $R_8$ represents —CH$_2$—CH$_2$OH, —CHOH—CH$_2$OH, —CH—(CH$_2$OH)$_2$, —CH$_2$—(CHOH)$_p$—CH$_2$OH with p=1 to 4 or —C—(CH$_2$OH)$_3$.

Preferentially, the complex of formula (XI) is chosen from the complexes between a ligand of formulae (XI') and (XI"):

(XI′)

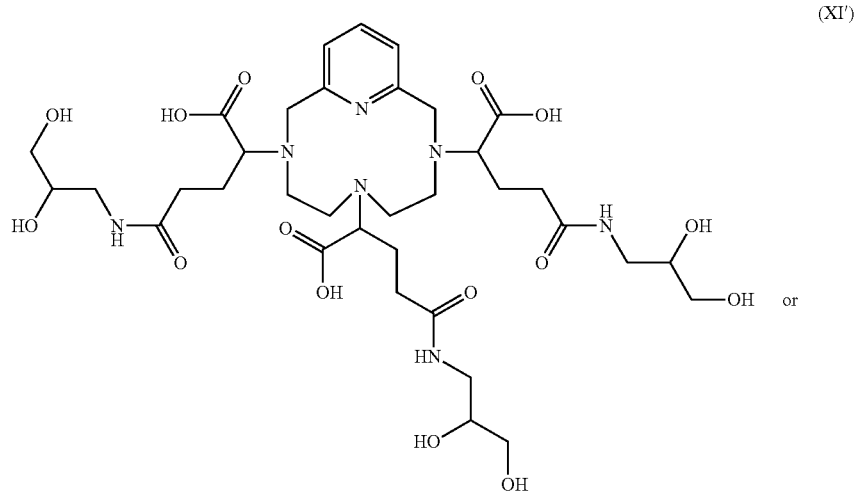

or (XI″)

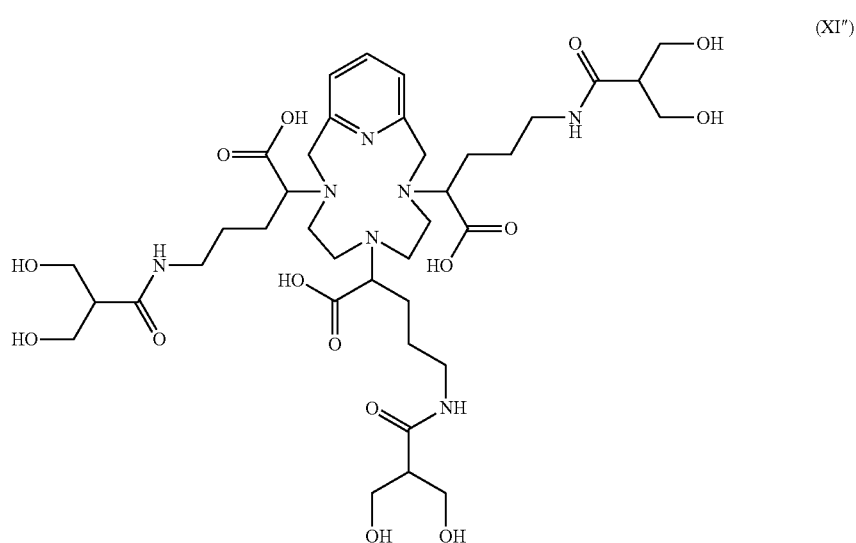

and a paramagnetic metal ion M.

Advantageously, the paramagnetic metal ion M is chosen from the ions of a paramagnetic metal with an atomic number of 21-29, 42-44 or 58-70, that is to say from scandium (Sc), titanium (Ti), vanadium (V), chromium (Cr), manganese (Mn), iron (Fe), cobalt (Co), nickel (Ni) or copper (Cu) ions or molybdenum (Mo), technetium (Tc) or ruthenium (Ru) ions or cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm) or ytterbium (Yb) ions. The paramagnetic metal ion M is preferably chosen from manganese, iron and lanthanide ions, more preferentially chosen from $Mn^{2+}$ and $Fe^{3+}$ ions and gadolinium ions such as $Gd^{3+}$ and even more preferentially chosen from lanthanide ions and in particular gadolinium ions such as $Gd^{3+}$.

Preferentially, the complexes of nonionic macrocyclic chelate with a paramagnetic metal are chosen from the complexes of nonionic macrocyclic chelate with a gadolinium ion (such as $Gd^{3+}$). More preferably, the complexes of nonionic macrocyclic chelate with a gadolinium ion are chosen from Gd-HP-DO3A, Gd-BT-DO3A and a complex of formula (XI) mentioned above in which M is a gadolinium ion. Even more preferentially, the complexes of nonionic macrocyclic chelate with a gadolinium ion are chosen from Gd-BT-DO3A and a complex of formula (XI) mentioned above in which M is a gadolinium ion.

Preferentially, the complex of formula (XI) mentioned above in which M is a gadolinium ion is chosen from the complexes of formula:

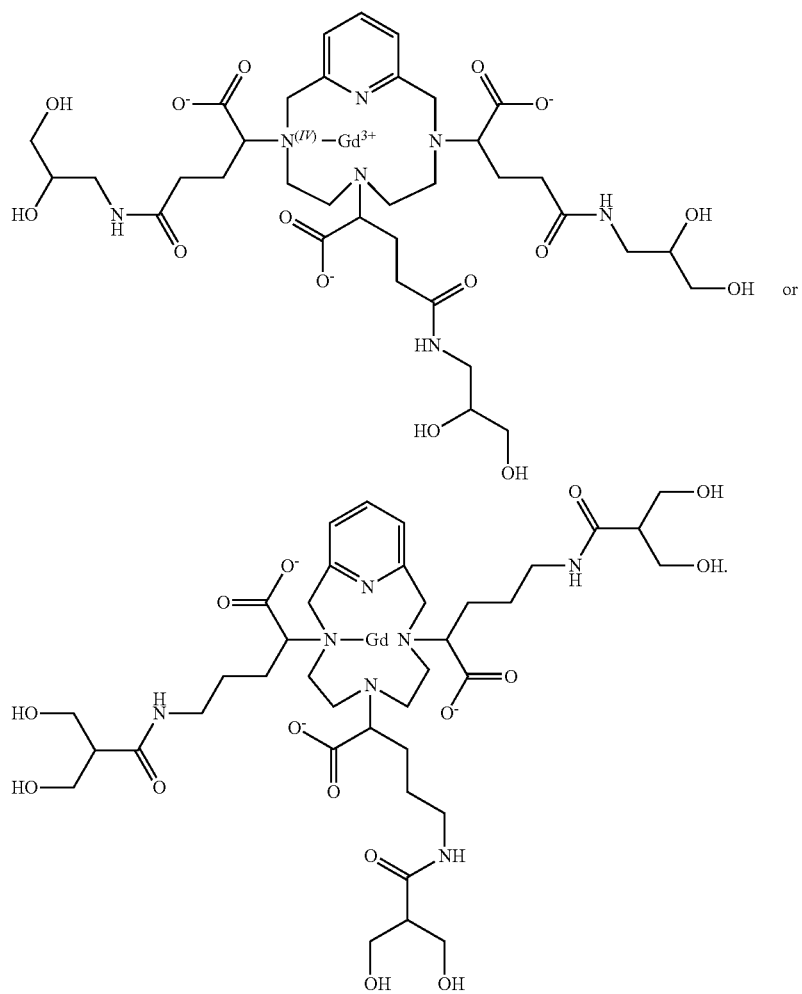

The processes for synthesizing these complexes of formula (XI) are well known to those skilled in the art, and are in particular described in document EP 1 931 673. These complexes of formula (XI) can be formulated with, for example, a calcium complex of DOTA as described in document WO 2014/174120.

In one advantageous embodiment, the aqueous phase can also comprise, as densifying agent, a nonionic iodinated contrast product up to 70% by volume relative to the total volume of densifying agent present in the composition. The nonionic iodinated contrast product that can be used as densifying agent in combination with the complex of non-ionic macrocyclic chelate with a paramagnetic metal is preferably chosen from iobitridol (Xenetix®), iopamidol (Iopamiron®, Isovue®), iomeprol (Iomeron®), ioversol (Optiray®, Optiject®), iohexol (Omnipaque®), iopentol (Imagopaque®), ioxitol (Oxilan®), iopromide (Ultravist®), metrizamide (Amipaque®), iosarcol (Melitrast®), iotrolan (Isovist®), iodixanol (Visipaque®), iosimenol and iosimide (Univist®) and a mixture thereof. Iobitridol is the preferential nonionic iodinated product. The Xenetix® 250, Xenetix® 300 and Xenetix® 350 products have densities of 1.28, 1.34 and 1.40, respectively. These iodinated contrast products have the advantage of allowing good solubility of the anti-cancer agent in the aqueous phase and of not destabilizing the emulsion. Preferentially, the composition comprises, as densifying agent, between 30% and 50% by volume of a complex of nonionic macrocyclic chelate with a paramagnetic metal and between 50% and 70% by volume of a nonionic iodinated contrast product, these percentages being specified relative to the total volume of densifying agent in the composition.

The use of ionic iodinated contrast products such as ioxaglic acid (Hexabrix®) or meglumina and/or sodium diatrizoate (Hypaque®, Gastrografin®, Gastroview® or Urografin®) is not indicated since these contrast products have the drawback of reducing the solubility of the anti-cancer agent in the aqueous phase, or even of preventing the dissolution thereof and/or of increasing the osmolality of the compositions.

In another advantageous embodiment (which may or may not be combined with the embodiment above in which the aqueous phase comprises as densifying agent a certain proportion of nonionic iodinated contrast product), the lipid phase may also comprise at least one non-iodized oil having a density of less than 1, preferably a non-iodized oil having a density of less than 0.96, even more preferentially a non-iodized oil chosen from linseed oil, soybean oil, palm oil, coconut oil, caster oil, corn oil, cottonseed oil, peanut oil, sesame oil, sunflower oil, safflower oil, almond oil, olive oil, poppy oil and an oil comprising or consisting of a mixture of fatty acid triglycerides of formula:

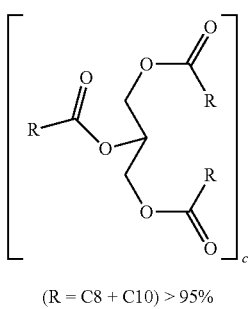

(R = C8 + C10) > 95% wherein R is an aliphatic chain comprising from 3 to 35 carbon atoms, with the proviso that more than 95% of said fatty acids are C8 and/or C10, sold for example under the name Miglyol®, for example the oil Miglyol® 810, the oil Miglyol® 812 (caprylic/capric triglyceride), the oil Miglyol® 818 (caprylic/capric/linoleic triglyceride), the oil Miglyol® 612 (glyceryl trihexanoate) or other propylene glycol dicaprylate dicaprate Miglyol® derivatives. The expression (R=C8+C10)>95% signifies that the triglycerides of the mixture are triglycerides of fatty acids of which more than 95% are C8 and/or C10 fatty acids (capric or caprylic acid). When the fatty acid is a C8 fatty acid, R is a chain comprising 7 carbon atoms and when the fatty acid is a C10 fatty acid, R is a chain comprising 9 carbon atoms.

The densities of the various non-iodized oils listed are specified in the following table:

| Oil name | Density |
| --- | --- |
| Linseed oil | 0.94 |
| Soybean oil | 0.92 |
| Miglyol ® oil | 0.94 |
| Palm oil | 0.90 |
| Coconut oil | 0.92 |
| Caster oil | 0.96 |
| Corn oil | 0.90 |
| Cottonseed oil | 0.92 |
| Peanut oil | 0.92 |
| Sesame oil | 0.92 |
| Sunflower oil | 0.93 |
| Safflower oil | 0.92 |
| Almond oil | 0.91 |
| Olive oil | 0.915 |
| Poppy oil | 0.928 |

In this precise embodiment, the density of the lipid phase comprising the iodized oil and one or more non-iodized oils as defined above is then preferentially from 0.9 to 1.2, more preferentially from 0.95 to 1.10, even more preferentially 1.05.

The size of the aqueous phase droplets is preferentially included from 1 to 200 µm, more preferentially included from 5 to 100 µm, even more preferentially included from 5 to 50 µm, or even from 5 to 10 µm. This size even further improves the stability of the emulsion. The size can be measured using an optical microscope (for example, the Leica DM2000 LED microscope).

Preferentially, the aqueous phase droplets are uniformly distributed. The uniformity is verified using an optical microscope: if aggregates of droplets are observed, these droplets are not uniformly distributed.

The aqueous phase/lipid phase volume ratio in the composition in the form of an emulsion according to the invention is advantageously from 1/2 (i.e. 0.5) to 1/4 (i.e. 0.25), preferentially from 2/5 (i.e. 0.4) to 3/10 (i.e. 0.3), more preferentially 1/3 (i.e. approximately 0.33). A ratio of less than 1/2 makes it possible to definitely obtain a W/O emulsion. Indeed, a 1/1 ratio between the lipid phase and the aqueous phase naturally promotes an O/W sense. In order to force the W/O sense, the amount of iodized oil added must be increased. Above a 1/4 ratio, the risk of embolism becomes significant. This is because, in order to dissolve a therapeutically effective amount of anti-cancer agent in the aqueous phase, it is necessary for this aqueous phase to have a sufficient volume. Having a lipid phase comprising an iodized oil and which is more than 4 times greater in volume than the aqueous phase generally results in the dose of iodized oil used becoming greater than the authorized limit. In the legal notices regarding a product such as Lipiodol®, it is indicated that the volume injected in an interventional radiology procedure must not exceed 15 ml.

The volume percentages of aqueous and lipid phases and the aqueous phase/lipid phase volume ratio of the composition in the form of an emulsion according to the invention make it possible to systematically obtain an inverse (W/O) emulsion which makes it possible to improve the conveying of an anti-cancer agent into a tumor.

Advantageously, the composition according to the invention has a viscosity at 20° C. included from 100 to 200 mPa·s, preferentially included from 120 to 170 mPa·s, more preferentially included from 150 to 165 mPa·s, and/or a viscosity at 37° C. included from 40 to 80 mPa·s, preferentially included from 50 to 70 mPa·s, more preferentially included from 60 to 70 mPa·s. The viscosity values are obtained using a Malvern Instruments Kinexus Pro rheometer, having a 4° cone-plate cell with a diameter of 40 mm. The measurements are carried out at an imposed stress in a range of from 0.16 to 10 Pa.

Iodized Oils

The term "fatty acid" is intended to denote saturated or unsaturated, aliphatic carboxylic acids having a carbon-based chain of at least 4 carbon atoms. Natural fatty acids have a carbon-based chain of 4 to 28 carbon atoms (generally an even number). The term "long-chain fatty acid" is used for a length of 14 to 22 carbons and the term "very-long-chain fatty acid" is used if there are more than 22 carbons. Conversely, the term "short-chain fatty acid" is used for a length of 4 to 10 carbons, especially 6 to 10 carbon atoms, in particular 8 or 10 carbon atoms. Those skilled in the art know the associated nomenclature and in particular use:

Ci–Cp to denote a range of Ci to Cp fatty acids,
Ci+Cp, the total of the Ci fatty acids and of the Cp fatty acids.

For example:
the fatty acids having 14 to 18 carbon atoms are written as "C14-C18 fatty acids",
the total of the C16 fatty acids and of the C18 fatty acids is written as C16+C18;
for a saturated fatty acid, a person skilled in the art will use the following nomenclature Ci:0, wherein i is the number of carbon atoms of the fatty acid. Palmitic acid will for example be denoted by the nomenclature (C16:0);
for an unsaturated fatty acid, a person skilled in the art will use the following nomenclature Ci:x n-N where N will be the position of the double bond in the unsaturated fatty acid starting from the carbon opposite the acid group, i is the number of carbon atoms of the fatty acid, and x is the number of double bonds (unsaturations) of this fatty acid. Oleic acid will for example be denoted by the nomenclature (C18:1 n-9).

Advantageously, the iodized oil according to the invention comprises or consists of derivatives of iodized fatty acids, preferentially of ethyl esters of iodized fatty acids, more preferentially of ethyl esters of iodized fatty acids of poppy oil, of olive oil, of rapeseed oil, of peanut oil, of soybean oil or of walnut oil, even more preferentially of ethyl esters of iodized fatty acids of poppy oil or of olive oil. More preferentially, the iodized oil according to the invention comprises or consists of ethyl esters of iodized fatty acids of poppy oil (said poppy also being known as blue seeded opium poppy or *Papaver somniferum* var. *nigrum*). The poppy oil, also known as poppyseed oil, preferentially contains more than 80% of unsaturated fatty acids (in particular of linoleic acid (C18:2 n–6) and of oleic acid (C18:1 n–9)) of which at least 70% of linoleic acid and at least 10% of oleic acid. The iodized oil is obtained from complete iodization of an oil such as poppy oil under conditions which allow bonding of one iodine atom for each double bond of the unsaturated fatty acids (Wolff et al. 2001, Medicine 80, 20-36) followed by trans-esterification.

The iodized oil according to the invention preferentially contains from 29% to 53% (w/w), more preferentially 37% to 39% (w/w), of iodine.

As examples of iodized oils, mention may be made of Lipiodol®, Brassiodol® (derived from rapeseed (*Brassica compestis*) oil), Yodiol® (derived from peanut oil), Oriodol® (derived from poppy oil but in the form of fatty acid triglycerides) and Duroliopaque® (derived from olive oil).

Preferentially, the iodized oil is Lipiodol®, which is an iodized oil used as a contrast product and in certain interventional radiology procedures. This oil is a mixture of ethyl esters of iodized and non-iodized fatty acids of poppyseed oil. It consists mainly (in particular, of more than 84%) of a mixture of ethyl esters of long-chain iodized fatty acids (in particular C18 fatty acids) derived from poppyseed oil, preferentially of a mixture of ethyl monoiodostearate and ethyl diiodostearate. The iodized oil may also be an oil based on a monoiodized ethyl ester of stearic acid (C18:0) derived from olive oil. A product of this type, called Duroliopaque® was sold a few years ago.

The main characteristics of Lipiodol® are the following:

| Compounds | Proportions in the fatty acid mixture |
|---|---|
| Ethyl palmitate (Ethyl C16:0) | 4.6% to 6.7% (w/w), preferentially 4.8% (w/w) |
| Ethyl stearate (Ethyl C18:0) | 0.8% to 1.9% (w/w), preferentially 1.2% (w/w) |
| Ethyl monoiodostearate | 11.3% to 15.3% (w/w), preferentially 13.4% (w/w) |
| Ethyl diiodostearate | 73.5% to 82.8% (w/w), preferentially 78.5% (w/w) |

| Other characteristics of Lipiodol ®: | |
|---|---|
| Iodine | 37% to 39% (w/w) (i.e. 480 mg/ml) |
| Viscosity | |
| at 37° C. | 25 mPa · s |
| at 20° C. | 50 mPa · s |
| Density | 1.268-1.290 g/cm³ at 20° C., preferentially 1.28 |

Preferentially, the amount of iodized oil present in the composition according to the invention does not exceed 15 ml.

Preferentially, the lipid phase consists essentially of iodized oil as defined above and of a surfactant of formula (I) or (I'). In one particular embodiment of the invention, the lipid phase consists essentially of iodized oil as defined above, of a non-iodized oil as defined above and of a surfactant of formula (I) or (I').

Anti-Cancer Agent

The anti-cancer agent vectorized by the composition according to the invention or included in the composition in the form of an emulsion according to the invention is preferentially chosen from anthracyclines, platinum complexes, anthracycline-related compounds such as mitoxantrone and nemorubicin, antibiotics such as mitomycin C (Ametycine®), bleomycin and actinomycin D, other antineoplastic compounds such as irinotecan, 5-fluorouracil (Adrucil®), sorafenib (Nevaxar®), sunitinib (Sutent®), regorafenib, brivanib, orantinib, linsitinib, erlotinib, cabozantinib, foretinib, tivantinib, fotemustine, tauromustine (TCNU), carmustine, cytosine C, cyclophosphonamide, cytosine arabinoside (or cytarabine), paclitaxel, docetaxel, methotrexate, everolimus (Afinitor®), PEG-arginine deiminase, the tegafur/gimeracil/oteracil combination (Teysuno®), muparfostat, peretinoin, gemcitabine, bevacizumab (Avastin®), ramucirumab, floxuridine, immunostimulants such as GM-CSF (granulocyte-macrophage colony-stimulating factor) and recombinant forms thereof: molgramostim or sargramostim (Leukine®), OK-432 (Picibanil®), interleukin-2, interleukin-4 and tumor necrosis factor-alpha (TNFalpha), $^{125}$I-labeled anti-CEA (carcinoembryonic antigen) antibodies, microspheres loaded with one of the above-mentioned compounds, radioelements, complexes of said radioelements with chelates, magnetic particles based on an iron compound (ultrasmall superparamagnetic particles of iron oxide or USPIOs) and/or on a gadolinium chelate, radioactive microspheres, nucleic acid sequences or a mixture of one or more of these compounds (preferentially a mixture of one or more anthracyclines or a mixture of an anthracycline and a radioelement, as mentioned above, or a mixture of an anthracycline and a particle based on an iron compound and/or on a gadolinium chelate.

Preferentially, the aqueous phase of the composition according to the invention comprises 0.5% to 2.5% (w/v), more preferentially 1% to 2% (w/v), of anti-cancer agent in the aqueous phase.

The composition in emulsion form may comprise one or more anti-cancer agents. Preferably, at least one anti-cancer agent is water-soluble, i.e. it is more than 50% soluble in the aqueous phase. Thus, when the composition in emulsion form comprises only one anti-cancer agent, said agent is preferably water-soluble and is therefore in the dispersed aqueous phase. When the composition in emulsion form comprises several anti-cancer agents, some of them may be in the continuous lipid phase.

The preferential anti-cancer agent is chosen from anthracyclines, mitomycin C, platinum complexes, radioelements and the complexes thereof listed above. The anti-cancer agent is more preferentially chosen from anthracyclines and even more preferentially from doxorubicin, epirubicin, nemorubicin and idarubicin.

Advantageously, the anti-cancer agent is chosen from intercalating agents such as doxorubicin, epirubicin, idarubicin, nemorubicin, mitoxantrone and pirarubicin; alkylating agents such as cisplatin, carboplatin, oxaliplatin, lobaplatin, cyclophosphonamide and mitomycin C, fotemustine; topoisomerase type 1 inhibitors such as irinotecan; topoisomerase type 2 inhibitors such as doxorubicin and mitoxantrone; tyrosine kinase inhibitors such as everolimus; multikinase inhibitors such as sorafenib, antimetabolite agents such as 5-fluorouracil, methotrexate and gemcitabine, the radioelements as listed above, complexes of these radioelements with macrocyclic chelates, magnetic particles based on an iron compound, radioactive microspheres, nucleic acid sequences and a mixture thereof.

Preferentially, the anthracyclines mentioned above are chosen from doxorubicin (or adriamycin sold under the name Adriblastine® by Pfizer), epirubicin (Farmorubicin®), idarubicin (Zavedos®), daunorubicin, pirarubicin, nemorubicin and a mixture of one or more of these compounds.

Preferentially, the platinum complexes mentioned above are chosen from cisplatin (Platinol AQ®), carboplatin, miriplatin, oxaliplatin (Eloxatine®), lobaplatin and a mixture of one or more of these compounds.

Preferentially, the radioelements mentioned above are chosen from rhenium 186 ($^{186}$Re), rhenium 188 ($^{188}$Re), yttrium 90 ($^{90}$Y), lutetium 177 ($^{177}$Lu), holmium 166 ($^{166}$Ho), iodine 125 ($^{125}$I), iodine 131 ($^{131}$I), phosphorus 32 ($^{32}$P), strontium 89 ($^{89}$Sr), samarium 153 ($^{153}$Sm), copper 67 ($^{67}$Cu), tin 117m ($^{117m}$Sn), bismuth 213 ($^{213}$Bi), bismuth 212 ($^{212}$Bi), astate 211 ($^{211}$At), radium 223 ($^{223}$Ra), indium 111 ($^{111}$In), gallium 67 ($^{67}$Ga), gallium 68 ($^{68}$Ga), metastable technetium 99 ($^{99m}$Tc) and a mixture of one or more of these compounds. The radioelement, optionally in a form complexed with linear or macrocyclic chelates, is preferentially chosen from $^{188}$Re, $^{90}$Y, $^{177}$Lu, $^{166}$Ho, $^{131}$I, $^{111}$In, $^{67}$Ga, $^{68}$Ga and 99mTc or even more preferentially from $^{188}$Re, $^{90}$Y, $^{177}$Lu, $^{166}$Ho and $^{131}$I. Preferentially, the chelates of the complexes of these radioelements mentioned above are chosen from linear chelates and macrocyclic chelates such as DOTA, PCTA, DTPA, NOTA, and derivatives thereof, more preferentially from macrocyclic chelates such as DOTA, PCTA, NOTA, and derivatives thereof. Yttrium 90 ($^{90}$Y) and the complexes of yttrium 90 and of macrocyclic chelates as defined above are preferential compounds in their respective categories.

Preferentially, the nucleic acid sequences mentioned above are chosen from deoxyribonucleic acid (DNA) and ribonucleic acid (RNA) sequences, more preferentially chosen from DNA or RNA sequences vectorized by gene therapy vectors, such as viral vectors chosen from adenovirus (DNA virus) vectors, retrovirus (RNA virus) vectors, vectors derived from adeno-associated viruses or AAVs and vectors derived from other viruses (such as Herpes Simplex viruses (HSVs), poxviruses, influenza viruses), and nonviral vectors such as polycations or nanoparticles (in particular of hydroxyapatite or modified hydroxyapatite (such as poly-L-lysine (PLL)-modified hydroxyapatite)) and interfering RNA (siRNA for small interfering RNA) or double-stranded RNA (dsRNA) sequences.

The nucleic acid sequences are preferentially chosen from the native or modified sequences or a part of the native or modified sequences of the gene encoding the p53 protein, encoding the Rb protein (in particular the Rb1 gene) or encoding the gene encoding interleukin 12 (IL-12), or the respective transcripts thereof (i.e. in RNA form).

The commercial form of these anti-cancer agents is usually the lyophilized form or the pulverized form (i.e. in powder form). These lyophilisates or powders of anti-cancer agents may contain the excipients conventionally used in the pharmaceutical field: lactose (dissolving and lyophilizing agent), methyl para-hydroxybenzoate (antioxidant) and/or sodium chloride (NaCl).

For the purposes of the present description, the term "particles based on an iron compound" is intended to mean particles comprising or consisting of an iron compound, generally comprising iron (III), generally an iron oxide or hydroxide. The term ultra small particles of iron oxide or USPIOs is often used.

As a general rule, the magnetic particles are totally or partly composed of iron hydroxide; of iron oxide hydrate; of ferrites; of mixed iron oxides such as mixed iron oxides of cobalt, of nickel, of manganese, of beryllium, of magnesium, of calcium, of barium, of strontium, of copper, of zinc or of platinum; or a mixture thereof.

According to one particularly preferred variant, the magnetic particles are superparamagnetic.

The magnetic particles before being covered with the appropriate coating, then preferably have a crystal diameter of from 5 to 200 nm, even better still from 10 to 60 nm or from 10 to 20 nm.

In one advantageous embodiment, the magnetic particles based on an iron compound are covered with a hydrophilic compound, preferentially of polyethylene glycol (PEG) type, more preferentially a PEG having a molar mass included from 1500 to 3000.

In another advantageous embodiment, the magnetic particles based on an iron compound are covered with an unsaturated, preferentially monounsaturated, fatty acid, even more preferentially with oleic acid (C18:1 n–9). The magnetic particles thus made liposoluble are suspended in the continuous lipid phase.

For the purposes of the present application, the term "ferrite" denotes iron oxides of general formula [x $Fe_2O_3$, y $MO_z$], wherein M denotes a metal that can be magnetized under the effect of a magnetic field, such as Fe, Co, Ru, Mg or Mn, it being possible for the magnetizable metal to be optionally radioactive.

Preferentially, the magnetic particles of the compositions of the invention comprise a ferrite, in particular maghemite ($\gamma$ $Fe_2O_3$) or magnetite ($Fe_3O_4$), or else mixed ferrites of cobalt ($Fe_2CoO_4$) or of manganese ($Fe_2MnO_4$). In this context, preference is most particularly given to the magnetic particles totally or partly composed of a ferrite, and preferably essentially (i.e. more than 90%, preferentially more than 95%, even more preferentially more than 98% by weight), of maghemite or of magnetite or of a mixture thereof.

Preferentially, the radioactive microspheres mentioned above consists of a cation exchange resin (comprising for example a polyvinyl alcohol or a copolymer comprising styrene and divinylbenzene, such as Aminex 50W-X4 from the company Biorad) labeled with yttrium 90 (SIR-Spheres® sold by the company SIRTeX Medical Ltd) or consists of glass into which yttrium 90 has been incorporated (TheraSphere® sold by the company BTG) or consists of a polymer such as polylactic acid (PLLA) and of one of the radioelements mentioned above, holmium (166Ho) then being the preferred radioelement. More preferentially, it is yttrium in the form of $^{89}Y_2O_3$ which is incorporated into the microspheres consisting of glass, said microspheres then being irradiated with neutrons in order to make them radioactive by converting the cold yttrium $^{89}$Y to radioactive yttrium $^{90}$Y. Even more preferentially, the microspheres consisting of a cation exchange resin or consisting of glass have respectively a diameter of from 20 to 60 µm and from 20 to 30 µm. The microspheres of the SIR-Spheres type were in particular the subject of patent EP 0 740 581 B1.

Preferentially, the microspheres loaded with one of the compounds mentioned above are loaded with an anthracycline such as doxorubicin, epirubicin or idarubicin or with a topoisomerase type I inhibitor such as irinotecan or with a platinum complex such as cisplatin. These microspheres are preferentially produced from polyvinyl alcohol (PVA). Preferentially, they consist of a hydrogel of PVA and more preferentially consist of a polymer of PVA modified with sulfonate $SO_3^-$ groups to which the compounds mentioned above attach when they are positively charged (DC Beads®, DC-Beads M1® and LC-Beads® sold by the company Biocompatibles) or they are produced from monomers such as vinyl acetate and methyl acrylate which, when they are combined together, form a PVA/acrylic copolymer (copolymer of poly(sodium acrylate-co-vinyl alcohol)) modified with carboxylate COO— groups to which the compounds mentioned above attach, by simple ionic bonding, when they are positively charged (Hepasphere® or Quadrasphere® sold by Merit Medical). These microspheres can also consist of a polyphosphazene polymer and are then loaded with doxorubin, with epirubicin, with idarubicin or with irinotecan (Embozene Tandem® microspheres sold by the company Celonova Biosciences). They can also consist of a polymer obtained from hydrolyzed potato flour crosslinked and substituted with glycerol ether groups, and are then loaded with doxorubicin, actinomycin D, tauromustine, cisplatin, carboplatin, mitomycin C, fotemustine, carmustine, irinotecan, 5-FU, floxuridine or docetaxel, with $^{125}$I-labeled anti-CEA (carcinoembryonic antigen) antibodies or with 99mTc-DTPA complex (Embocept® S microspheres sold by Pharmacept).

Surfactant

It is recalled that the term "surfactant" refers to a composition with an amphiphilic structure which confers thereon a particular affinity for interfaces of water/oil type, thereby giving it the ability to lower the free energy of these interfaces and to stabilize dispersed systems.

The composition according to the invention comprises at least one surfactant of formula (I) or (I') as defined above. It can therefore comprise a surfactant of formula (I) or (I') or a mixture of surfactants of formula (I) or (I').

The surfactant has the formula (I) or (I') as defined above, preferably in which s is 0 or 1, m represents an integer from 2 to 10 and $R_1$ represents a group of formula (II) as defined above, in which n represents an integer from 5 to 7, o represents an integer from 1 to 3, p represents an integer from 3 to 5, q represents an integer from 2 to 5 and r is 0 or 1. Even more preferentially, in formula (I) or (I') as defined above, s is 1, m represents an integer from 2 to 5 and n is 7, o is 1, p is 5 and q represents an integer from 2 to 4 and r is 1 in formula (II) represented by $R_1$.

The HLB (meaning hydrophilic-lipophilic balance) is a magnitude, well known to those skilled in the art, characteristic of a surfactant. Preferentially, the surfactant according to the invention is a surfactant with a low HLB, i.e. a surfactant having an HLB value included from 1 to 8, preferentially included from 1 to 6. The HLB makes it possible to determine the type of oil-in-water or water-in-oil emulsion, as illustrated in the article by W. C. Griffin ("Classification of Surface-active agents by "HLB"", Journal of the Society of Cosmetic Chemists, 1949, 311-326). This article indicates in particular that, for surfactants of which the HLBs are from 4 to 6, emulsions of W/O type are observed, while for surfactants of which the HLBs are from 8 to 18, emulsions of O/W type are instead observed.

Advantageously, the surfactant of formula (I) or (I') is soluble in the iodized oil, in particular in the proportion ranges indicated above.

Advantageously, the surfactant of formula (I) or (I') according to the invention is chosen from polyglyceryl polyricinoleate and PEG-30 dipolyhydroxystearate.

Polyglyceryl polyricinoleate or PGPR (Palsgaard®4125, Palsgaard®4150, Palsgaard®4110, Palsgaard®4120 or Palsgaard®4175) is a surfactant which has, as hydrophilic group, polyglycerol (preferably consisting of at least 75% of di- and triglycerol and of at most 10% of heptaglycerol) and, as hydrophobic group, interesterified ricinoleiques fatty acids. It has an HLB of 1.5.

It corresponds to a surfactant of formula I, as defined above, in which:

s is 1,
m represents an integer from 2 to 5,
$R_1$ represents a group of formula (II) as defined above, in which n is 7, o is 1, p is 5, q is 2 to 4 and r is 1,
$R_2$ represents $R_1$ and/or a hydrogen atom.

Preferentially, the surfactant of formula (I) or (I') is a mixture of surfactants of formula (I) or (I') in which:

s is 1,
m is 2, 3, 4 or 5,
$R_1$ represents a group of formula (II) as defined above, in which n is 7, o is 1, p is 5, q is 2, 3 or 4 and r is 1,
$R_2$ represents $R_1$ and/or a hydrogen atom.

Preferentially, the surfactant of formula (I) or (I') according to the invention is a mixture of surfactants, chosen from the compounds of formula:

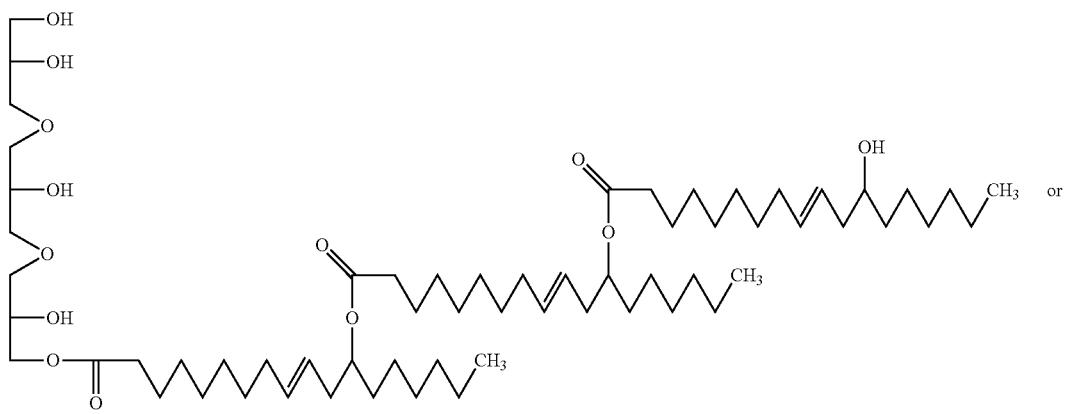

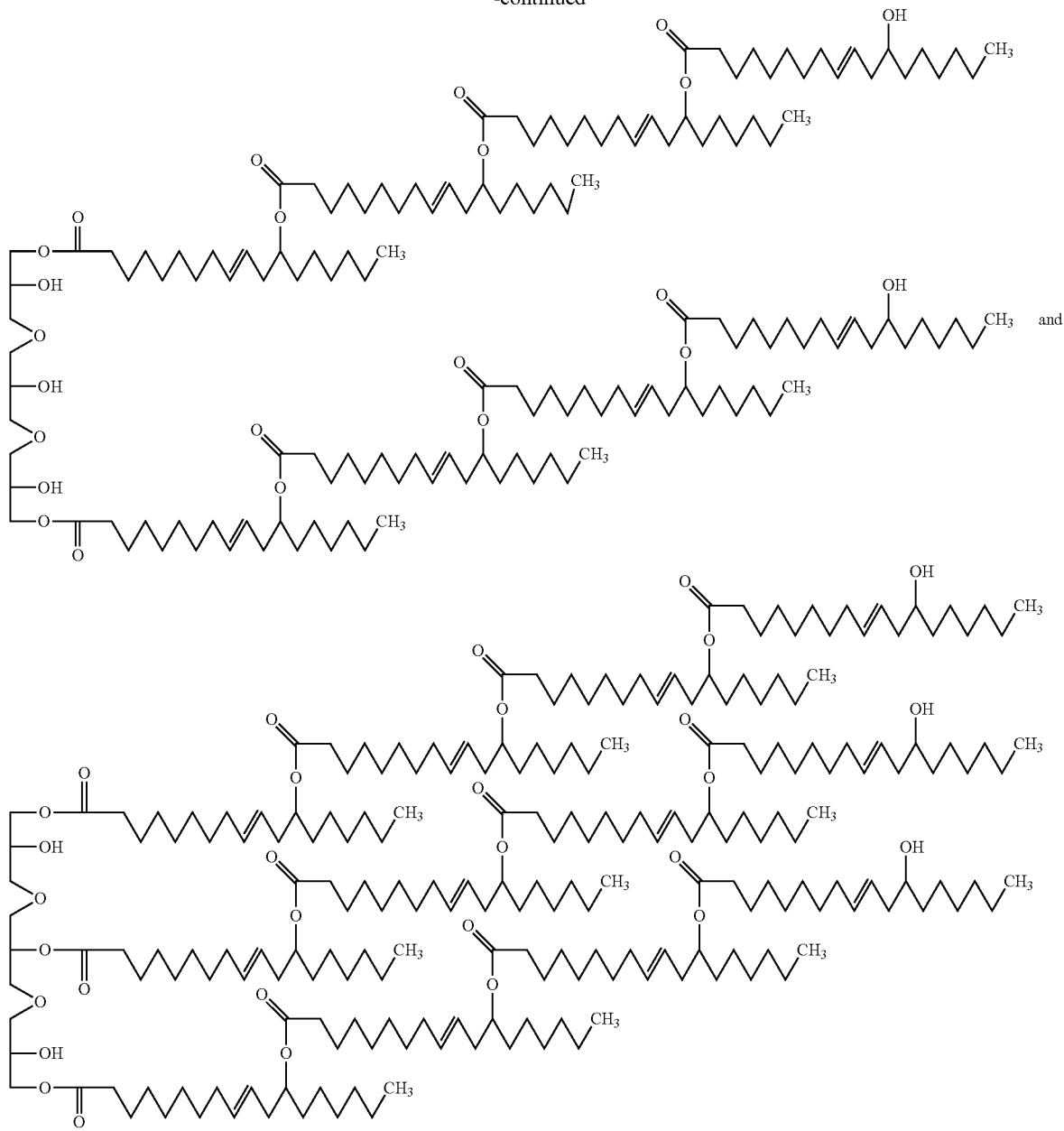

PEG-30 dipolyhydroxystearate (Cithrol® DPHS and formerly Arlacel® P135 sold by the company Croda) as an HLB of 5-6. The name PEG is in accordance with the nomenclature conventions set by the INCI, the value 30 specified above corresponding to the average number of ethylene oxide monomer units.

It corresponds to a surfactant of formula 1, as defined above, in which:
s is 0,
m is 30,
$R_1$ represents a group of formula (II) as defined above, in which n is 9, o is 1, p is 5, q is 7 and r is 0,
$R_2$ is identical to $R_1$.

Use of the Composition According to the Invention

According to a second subject, the invention relates to the use of the composition as defined above, for vectorizing an anti-cancer agent. The invention also relates to a composition in emulsion form as defined above, for use thereof in the treatment of cancer or metastases thereof, preferentially by transarterial chemoembolization. In one advantageous embodiment, the invention relates to the use of a composition according to the invention, for preparing a medicament for treating cancer or metastases thereof, preferentially by transarterial chemoembolization. Transarterial chemoembolization is defined as the transarterial percutaneous introduction of a substance in order to obstruct a blood vessel in combination with an anti-cancer agent, in order to deliver a therapeutically effective amount of this agent into a tumor. Preferentially, the cancer thus treated is chosen from liver cancer (in particular primary liver cancer, such as hepatocellular carcinoma or HCC), cholangiocarninoma, hepatic metastases of primary cancers chosen from colorectal cancer, neuroendocrine tumors, breast cancers, kidney cancers and melanomas.

The chemoembolization of an hepatic tumor is preferentially carried out by implementing the following successive steps:

a) percutaneous catheterization from the femoral artery, b) administration of the emulsion according to the invention until stasis is observed in the second-order or third-order branches, c) optionally, administration of an embolizing agent in the tumor after the emulsion has been administered.

Preferentially, the emulsion according to the invention thus administered comprises no more than 20 ml of iodized oil, more preferentially no more than 15 ml of iodized oil.

The catheterization, which consists in bringing a tube, called a catheter, into the hepatic artery and then into the branch of this artery which perfuses the cancerous lesion, is advantageously carried out with the assistance of an imaging technique. Interventional radiologists are moreover provided with guidance software in order to enable them to place their catheter as optimally as possible.

The term "embolizing agent" is intended to mean one or more compounds which make it possible to slow down or stop, definitively or temporary, the blood flow in a vessel. As examples of an "embolizing agent", mention may be made of the gelatin sponge, gelatin foam particles (Gelfoam®, Spongel®, Curaspon®), polyvinyl alcohol (PVA) or calibrated microspheres based, for example, on trisacrylgelatin, on PVA (Ivalon®, Contour®), etc.

Advantageously, before the chemoembolization procedure, an angiography or arteriography, carried out using an angioscan or an MR angio (magnetic resonance angiography or MRA), and usually an injection of contrast product (for example, for the angioscan: water-soluble iodinated contrast products such as iobitridol (Xenetix®) or iohexol (Omnipaque®), and for the MR angio: gadolinium chelates such as gadoteric acid (Dotarem®) or gadobutrol (Gadovist®)), is performed in order to pinpoint the visceral vascularization and the arterial perfusion of the tumor(s).

This chemoembolization technique can be used alone or in combination with one or more other techniques mentioned below. It can also be replaced with one of these other techniques.

When the anti-cancer agent is chosen from radioelements or complexes of radioelements with macrocyclic chelates mentioned above, the technique used is internal selective radiotherapy or radioembolization. It consists in injecting the composition according to the invention directly into the branch of the hepatic artery which perfuses the tumor. This technique has the advantage of delivering a very significant irradiation to the tumor without, however, significantly irradiating the healthy liver and the other organs of the patient.

When the anti-cancer agent is chosen from magnetic particles based on an iron compound (USPIOs), the technique used is magnetic hyperthermia ablation. This consists in inducing a local increase in temperature at the level of the tumor tissue, the tumor cells being more sensitive to an increase in temperature than healthy cells. This increase in temperature is caused by using an external stimulus and in particular the application of an alternating magnetic field to the area that it is desired to treat. Two types of hyperthermia are distinguished depending on the temperature reached: for temperatures above 46° C., it is possible to induce tissue necrosis and the term thermoablation is then used; temperatures of 42° C. to 46° C. modify the functions of numerous structural and enzymatic proteins, modifying cell development and differentiation and possibly inducing apoptosis, the term moderate hyperthermia is then used. If the cells do not die, they become more sensitive to ionizing radiation or to chemotherapy.

When the anti-cancer agent is a nucleic acid sequence chosen from sequences of deoxyribonucleic acid (DNA) and ribonucleic acid (RNA) vectorized by a viral vector or a non-viral vector as mentioned above or an interfering RNA (siRNA for small interfering RNA) or double-stranded RNA (dsRNA) sequence, the technique used is gene therapy, sometimes also called "genotherapy". The principle of this approach is to introduce a foreign gene of which the expression product induces (directly or indirectly) the death of the tumor cells. Schematically, three approaches can be used: a) the induction of an immune defense ("immunostimulation") by modifying the tumor cell membrane antigens; b) the transfer of a tumor "suppressor" gene into the genome of the tumor cell, or finally c) the transfer of a "suicide" gene which makes it possible to convert a nonactive anti-cancer agent prodrug into a molecule that is toxic to the tumor cells.

All these various techniques are known to those skilled in the art. The latter will know how to easily chose the parameters to be adjusted in order to carry out these techniques using the composition according to the invention.

Unless otherwise indicated, the terms "treating" and "treatment" are intended to mean any action aimed at improving the comfort, well-being and survival of an individual, this term therefore covering both attenuating, decreasing, relieving and curing.

Preparation of the Composition in the Form of an Emulsion According to the Invention The composition in emulsion form is preferentially prepared extemporaneously.

The invention also relates to a method for preparing a composition in emulsion form as defined above, comprising the following steps:

a) mixing the surfactant of formula (I) or (I') as defined above in the iodized oil, and b) mixing the solution obtained in step a) with an aqueous solution comprising an anti-cancer agent and a densifying agent chosen from the complexes of nonionic macrocyclic chelate with a paramagnetic metal described above.

The lipid phase prepared in step a) can also comprise a non-iodized oil as defined above.

The mixing carried out in step b) can be carried out by any means known to those skilled in the art. Preferentially, a three-way tap is used. The iodized oil comprising the surfactant is placed in a first syringe which is attached to the three-way tap. The aqueous solution comprising the anti-cancer agent is placed in a second syringe which is also attached to this three-way tap at 90°.

Mixing of the two phases is carried out by alternately pushing on the plungers of the two syringes (preferentially from 20 to 35 times). Preferentially, all of the mixture is passed through one syringe and then through the other every 1 to 2 seconds. The third channel of the tap makes it possible to attach a catheter which is selectively advanced, under fluoroscopic control, as far as the tumor lesion, for administration of the emulsion.

Preferentially, the preparation of the composition according to the invention is carried out at a temperature between 10 and 40° C., more preferentially between 20 and 30° C.

Marketing Forms for the Composition According to the Invention

The invention also relates to a kit comprising:
a surfactant of formula (I) or (I') as defined above,
an iodized oil, an anti-cancer agent,
a densifying agent chosen from the complexes of nonionic macrocyclic chelate with a paramagnetic metal mentioned above,
as combination products for use simultaneously, separately or spread out over time, for use thereof for treating cancer.

The surfactant, the iodized oil, the anti-cancer agent (the latter compound generally being in powder form) and the densifying agent (the latter compound generally being in liquid form) are in three different containers. A first container comprises the iodized oil to which the surfactant of formula (I) or (I') as defined above has been added. A second container comprises the anti-cancer agent in powder form. A third container comprises a solution comprising the densifying agent or the mixture of densifying agent mentioned above. For use of this kit, the anti-cancer agent in powder form is dissolved in the solution comprising the densifying agent. Generally, the mixing of the [surfactant/iodized oil and densifying agent/anti-cancer agent in aqueous solution] results in the composition in the form of an emulsion according to the invention.

Furthermore, the invention relates to a kit comprising:
a composition comprising the surfactant of formula (I) or (I') as defined above and an iodized oil,
a composition comprising an anti-cancer agent and a densifying agent chosen from the complexes of nonionic macrocyclic chelate with a paramagnetic metal,
as combination products for use simultaneously, separately or spread out over time, for use thereof for treating cancer.

The composition comprising the surfactant of formula (I) or (I') as defined above and an iodized oil and the composition comprising the anti-cancer agent and the densifying agent mentioned above (preferentially provided in liquid form) are in two different containers. Preferentially, the anti-cancer agent and the densifying agent mentioned above are dissolved in an aqueous solution extemporaneously or the day before the procedure. Preferably, the composition consists of a mixture of surfactant of formula (I) or (I'), of an iodized oil and optionally of a non-iodized oil. Generally, the mixing of the anti-cancer agent and the densifying agent mentioned above in aqueous solution results in the composition in the form of an emulsion according to the invention.

The term "container" is intended to denote any pharmaceutically acceptable receptacle which can contain a product. By way of example, mention may be made of an ampoule, a bottle or a prefilled syringe.

The term "pharmaceutically acceptable receptacle" is intended to denote any receptacle which does not interact with the product, preferentially any receptacle which does not release compounds into the iodized oil and does not degrade the iodized oil.

The examples which appear hereinafter are presented by way of nonlimiting illustration of the invention.

EXAMPLE 1

1. Preparation of Compositions in the Form of an Emulsion According to the Invention
    1.1. Emulsions of Lipiodol® and of Anthracycline
    50 mg of doxorubicin (Actavis) were reconstituted in 2.5 ml of gadobutrol (also called Gd-BT-DO3A and sold under the commercial name Gadovist® 1 mmol/ml by the company Bayer). After manual stirring for 30 seconds for good dissolution, the solution obtained was removed with a 20 ml luer lock syringe. This syringe was then placed on a three-way tap.

PGPR (1% w/v total, 100 mg—Interchim) was dissolved in 7.5 ml of Lipiodol® by manual stirring.

The oil obtained was removed with a 20 ml luer lock syringe, which was also placed on the three-way tap at 90° C. 34 passes, i.e. 17 back-and-forward motions, at medium force were carried out, beginning with the water into the oil.

For these emulsions, the volumes of the aqueous phase and of the lipid phase chosen were respectively 2.5 ml (i.e. 25% v/v) and 7.5 ml (i.e. 75% v/v). The aqueous phase/lipid phase ratio was ⅓.

Other emulsions were prepared:
by introducing no densifying agent, or
by replacing the Gadovist® densifying agent with the complex of nonionic macrocyclic chelate with a gadolinium ion of formula below

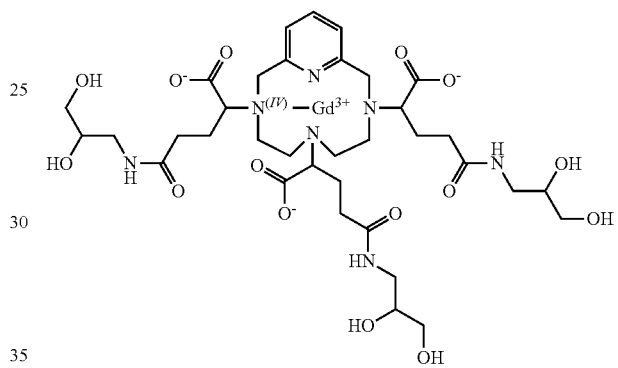

(called compound X below) or by replacing it with a densifying agent chosen from the iodinated contrast products (Xenetix® 250, Xenetix® 300 (300 mg of iodine/ml), Iopamiron® 350, Iopamiron® 300, Iomeron® 300, Ultravist® 300 or Omnipaque® 240),
by replacing the Gadovist® densifying agent with a mixture composed of 30% by volume of ProHance® and of 70% by volume of Xenetix® 350,
by replacing the surfactant PGPR with Cithrol™ DPHS (PEG-30 dipolyhydroxystearate).

For the Cithrol™ DPHS, dissolution was obtained by using ultrasound (Vial tweeter, 3×45 s) or by heating the iodized oil.

Verification of the Sense of the Emulsion:

Once the emulsion had been prepared, the sense thereof was verified by means of a simple visual test. Two bottles were prepared: one with physiological saline and the other with iodized oil (Lipiodol®).

A drop of freshly prepared emulsion was added to each of the two bottles. The drop dispersed in the bottle of Lipiodol® and did not disperse in the bottle of physiological saline; the emulsion was therefore indeed a W/O (water-in-oil) emulsion.

The red doxorubicin droplets were clearly visible in a yellow background of oil. The size of the aqueous phase droplets was evaluated using an optical microscope.

The principal emulsions prepared are described in the following table:

| Product number | Nature of the surfactant used | Proportion of surfactant used (% w/v) | Nature of the anti-cancer agent used | Nature of the densifying agent used | Sizes of the aqueous phase droplets | Visual stability observed* |
|---|---|---|---|---|---|---|
| E1 | PGPR | 1% | Doxorubicin | None | 5-40 μm | Phase separation <5% at 24 h |
| E2 | PGPR | 1% | Doxorubicin | Iobitridol** | 5-20 μm | No phase separation at 24 h |
| E3 | PGPR | 1% | Doxorubicin | Gadobutrol (Gadovist ®) | 5-10 μm | No phase separation at 24 h |
| E4 | PGPR | 1% | Doxorubicin | Compound X (see formula above) | 5-10 μm | No phase separation at 24 h |
| E5 | PGPR | 1% | Doxorubicin | 30% by volume of gadoteridol (ProHance ®) and 70% by volume of Iobitridol***** | 5-10 μm | No phase separation at 24 h |
| E6 | PGPR | 1% | Doxorubicin | Iobitridol*** | 5-20 μm | No phase separation at 24 h |
| E7 | PGPR | 1% | Doxorubicin | Iopamidol**** | 5-10 μm | No phase separation at 24 h |
| E8 | PGPR | 0.5% | Doxorubicin | Iobitridol** | 5-20 μm | No phase separation at 24 h |
| E9 | PGPR | 0.3% | Doxorubicin | Iobitridol** | 5-20 μm | No phase separation at 24 h |
| E10 | PGPR | 1% | Mitomycin C | Iobitridol** | 5-10 μm | No phase separation at 24 h |
| E11 | PGPR | 1% | Epirubicin | Iobitridol** | 5-20 μm | No phase separation at 24 h |
| E12 | PGPR | 0.7% | Idarubicin | Iobitridol** | 2-10 μm | No phase separation at 24 h |
| E13 | Cithrol ™ DPHS | 1% | Doxorubicin | None | 5-20 μm | Phase separation <5% at 24 h |
| E14 | Cithrol ™ DPHS | 1% | Doxorubicin | Iobitridol** | 5-20 μm | No phase separation at 24 h |
| E15 | Cithrol ™ DPHS | 1% | Doxorubicin | Iobitridol*** | 5-20 μm | No phase separation at 24 h |

*at ambient temperature (20° C.)
**Xenetix ® 250
***Xenetix ® 300
****Iopamiron ® 250
*****Xenetix ® 350

These various emulsions prepared using a surfactant of formula (I), various anti-cancer agents and densifying agents of different nature, all demonstrated a stability in accordance with expectations.

The replacement of the iodinated contrast products such as iobitridol and iopamidol, used as densifying agents, with complexes of nonionic macrocyclic chelate with a paramagnetic metal ion does not influence the stability of the emulsions obtained. By virtue of this replacement, it is possible to monitor the efficacy of the emulsions in accordance with the invention thus obtained by means of magnetic resonance imaging techniques such as MRI.

2. Comparison with Emulsions not in Accordance with the Invention

Emulsions according to the same protocol as that specified in paragraph 1.1 or a slightly different protocol (the differences compared with the protocol of paragraph 1.1 are indicated in the table below: the respective volumes of the aqueous and lipid phases are calculated on the basis of their ratio) were prepared using either a concentration of PGPR not in accordance with the invention, or surfactants having a low or high HLB, such as surfactants of the Span® family (fatty acid esters of sorbitan), or surfactants of the HCO family (hydrogenated and ethoxylated castor oil), such as HCO-10 (HLB=6.5) or HCO-60 (HLB=14) supplied by the company Nikko Chemicals, surfactants having a high HLB of the Cremophor® family (glycerol polyethylene glycol ricinoleate), of the Tween® family (polyoxyethylene fatty acid esters of sorbitan) or of the Pluronics® family (block copolymers based on ethylene oxides and propylene oxide, sold by BASF), and the Cithrol® PG32IS surfactant having a low HLB (HLB=6.7).

Densifying agents other than the complexes of nonionic macrocyclic chelate with a paramagnetic metal ion were tested, such as a complex of ionic chelate with a gadolinium ion (Gd-DTPA, sold under the name Magnevist®) or PVP (polyvinylpyrrolidone), glycerol, or else dextran T40 (Sigma), but the maximum amounts that can be used do not make it possible to approach the density of an iodized oil such as Lipiodol®.

The principal emulsions prepared are described in the following tables:

Emulsions Prepared with a Surfactant in Accordance with the Invention but Using a Surfactant Concentration which does not Comply and/or a Densifying Agent which does not Comply:

| Product number | Nature of the surfactant used | Proportion of surfactant used | Nature of the anti-cancer agent used | Aqueous phase/lipid phase ratio | Droplet sizes | Observations |
|---|---|---|---|---|---|---|
| E16 | PGPR | 0.2% by weight relative to the total volume of the emulsion | Doxorubicin 50 mg in 2.5 ml of Xenetix ® 250 | 1/3 | Heterogeneity: small drops and coarser drops of 20-50 μm | W/O emulsion Phase separation |
| E17 | PGPR | 0.2% by weight relative to the total volume of the emulsion | Doxorubicin 50 mg in 2.5 ml of physiological saline | 1/3 | Heterogeneity: small drops and coarser drops of 20-50 μm | W/O emulsion Phase separation |
| E18 | PGPR | 5% by weight relative to the total volume of the emulsion | Epirubicin 50 mg in 5 ml of water supplemented with 290 mg of glucose (5.8% w/v) | 1/1 | Heterogeneity: drops ranging from 5 to 50 μm | O/W emulsion total phase separation in 2 hours |
| E19 | PGPR | 1% by weight relative to the total volume of the emulsion | Doxorubicin 50 mg in 2.5 ml of Magnevist ® | 1/3 | Heterogeneity | W/O emulsion Phase separation |

Emulsions Prepared with a Surfactant and/or a Densifying Agent not in Accordance with the Invention and/or in Aqueous Phase/Lipid Phase Ratios which do not Comply:

| Product number | Nature of the surfactant used | Proportion of surfactant used by weight relative to the total volume of the emulsion | Nature of the anti-cancer agent used | Aqueous phase/lipid phase ratio | Droplet sizes | Observations |
|---|---|---|---|---|---|---|
| E20 | Span ® 80 | 1% (also tested: 0.5% and 0.8%) | 2 ml of a solution of doxorubicin 50 mg in 10 ml of Xenetix ® 250 | 1/4 or 1/3 | Aggregates of droplets of 50-100 μm | W/O emulsion Phase separation whatever the aqueous phase/lipid phase ratio and the proportion of surfactant used |
| E21* | Span ® 80 | 1% | 2 ml of a solution of doxorubicin 50 mg in 10 ml of physiological saline supplemented with dextan T40 at 2.5 g/50 ml | 1/4 | Heterogeneity: small drops and coarser drops of 20-50 μm | W/O emulsion Phase separation |
| E22* | Cremophor ® EL | 0.5% | 2 ml of a solution of doxorubicin 50 mg in 10 ml of physiological saline supplemented with dextan T40 at 3 g/50 ml | 1/4 | 2-5 μm | W/O emulsion Phase separation |
| E23 | Tween ® 80 | 0.1% | Doxorubicin (50 mg in 5 ml of Xenetix ® 250) | 1/1 | 10 μm | O/W emulsion Slight phase separation at 24 h |
| E24* | Tween ® 80 | 0.1% or 0.01% | Doxorubicin (50 mg in 5 ml of physiological saline supplemented with Tween ® 80 and 1% of PVP) | 1/1 | 10-100 μm | O/W emulsion |
| E25* | Tween ® 80 | 0.01% | Doxorubicin HCl in 5 ml of glycerol at 2.5% | 1/1 | 100-300 μm | O/W emulsion Immediate phase separation |

-continued

| Product number | Nature of the surfactant used | Proportion of surfactant used by weight relative to the total volume of the emulsion | Nature of the anti-cancer agent used | Aqueous phase/lipid phase ratio | Droplet sizes | Observations |
|---|---|---|---|---|---|---|
| E26' | Mixture of Tween® 80 and Span® 80 | 0.5% 0.5% | Doxorubicin (50 mg in 2.5 ml of Xenetix® 250) | 1/3 | Heterogeneity | Non-emulsified unstable system |
| E27 | CITHROL® PG32IS | 1% | Doxorubicin (50 mg in 2.5 ml of Xenetix® 250) | 1/3 | Not measurable | W/O emulsion Instant and violent phase separation |
| E28' | Pluronic® L101 | 5% | Doxorubicin (50 mg in 2.5 ml of water) | 1/4 | 10-100 μm | O/W emulsion Partial phase separation before 18 hours |
| E29 | HCO-10 | 1% | Doxorubicin (50 mg in 2.5 ml of Xenetix® 250) | 1/3 | | W/O emulsion Phase separation in 10 hours |
| E30 | HCO-60 | 1% | Doxorubicin (50 mg in 2.5 ml of Xenetix® 250) | 1/3 | | W/O emulsion Rapid phase separation |
| E31 | HCO-60 | 1% | Doxorubicin (50 mg in 5 ml of physiological saline) | 1/1 | | O/W emulsion |

*emulsion prepared with a densifying agent not in accordance with the invention: PVP (polyvinylpyrrolidone), Dextran T40, ioxaglic acid (Hexabrix®) or glycerol Emulsions Prepared without Surfactant and/or without Densifying Agent:

| Product number | Nature of the anti-cancer agent used | Aqueous phase/lipid phase ratio | Droplet sizes | Observations |
|---|---|---|---|---|
| E32* | Doxorubicin (50 mg in 5 ml of physiological saline) | 1/1 | 10 μm | O/W emulsion |
| E33 | Doxorubicin (50 mg in 5 ml of Xenetix® 250) | 1/1 | 10 μm | O/W emulsion |
| E34* | Doxorubicin (50 mg in 2.5 ml of Xenetix® 250) | 1/3 or 1/2 | Not measurable (greater than 200 μm) | W/O emulsion Immediate phase separation |
| E35* | Doxorubicin (50 mg in 3 ml of physiological saline) | 1/4 | 10 μm | O/W emulsion Very viscous and thick emulsion: not usable in a clinical context |
| E36 | Epirubicin (50 mg in 5 ml of Iopamiron® 250) | 1/1 | 10 μm | O/W emulsion |
| E37* | Epirubicin (50 mg in 5 ml of physiological saline) | 1/1 | 10-20 μm | O/W emulsion |

*emulsion prepared without densifying agent

Span® 80 (Croda) is sorbitan monooleate. Tween® 80 (Croda), also called polysorbate 80, is PEG-20 sorbitan monooleate. Cremophor® EL (BASF) has, as chemical name: polyoxyl 35 Castor Oil. Cithrol® PG32IS is polyglyceryl-3-diisostearate. It is not therefore branched like the surfactants of formula (I). HCO-10 (HLB=6.5) bears the INCI name: PEG-10 HYDROGENATED CASTOR OIL, while HCO-60 (HLB=14) bears the INCI name: PEG-60 HYDROGENATED CASTOR OIL.

Spans® other than Span® 80 (HLB=4.3) were tested: Span® 20 (HLB=8.6), Span® 65 (HLB=2.1), Span® 83 (HLB=3.7) and Span® 85 (HLB=1.8). The emulsions prepared with these surfactants all underwent phase separation immediately after they were prepared. The tests carried out with Pluronic® compounds (BASF) were also not conclusive since it was not possible to prepare an emulsion with these compounds.

Thus, all of the comparative emulsions obtained exhibited either insufficient stabilities, or a sense not in accordance with the invention, or were not visible (or were insufficiently visible) by magnetic resonance imaging techniques such as MRI.

The invention claimed is:

1. A composition in the form of a water-in-oil emulsion comprising:
from 20% to 40% (v/v) of aqueous phase, in the form of droplets, comprising an anti-cancer agent and a densifying agent selected from Gd-HP-DO3A, Gd-BT-DO3A, and a complex of formula (XI)

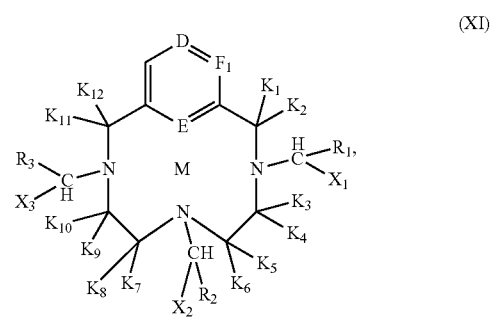

wherein:
M is a gadolinium ion;
$R_1$, $R_2$ and $R_3$ represent —COO$^-$;
E is N;

D represents CH;
F₁ represents CH;
X₁, X₂ and X₃ independently represent —(CH₂)ₙ—CO—NR₇R₈ or —(CH₂)ₙ—NR₇—CO—R₈, in which n is between 1 and 3, R₇ represents H or a methyl group, R₈ represents a $C_1$-$C_6$ hydroxyalkyl group; and
K₁ to K₁₂ each represent H;
from 60% to 80% (v/v) of lipid phase comprising an iodized oil and at least one surfactant of formula (I) in a proportion, by weight of surfactant relative to the total volume of the composition, of 0.3% to 5%, wherein formula (I) of said surfactant is the following:

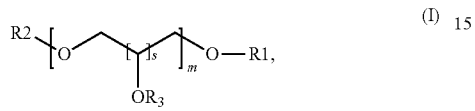

wherein:
s is 0 or 1;
m is an integer from 2 to 30;
R₁ represents a group of formula (II)

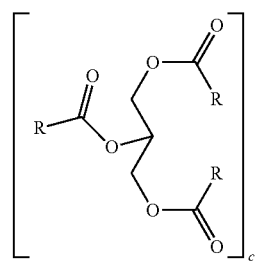

wherein n is an integer from 4 to 10, o is an integer from 1 to 4, p is an integer from 3 to 7, q is an integer from 2 to 10, and r is 0 or 1;
R₂ represents a hydrogen atom or an R₁; and
each R₃ independently represents a hydrogen atom or an R₁, and wherein the composition at 20° C. and at 1 bar and within 24 hours following its preparation, a visual phase separation of less than 5% by volume relative to the total composition is observed.

2. The composition of claim 1, wherein each R₃ of Formula (I) is a hydrogen atom.

3. The composition of claim 1, wherein the anti-cancer agent is selected from the group consisting of anthracyclines, platinum complexes, mitoxantrone, nemorubicin, mitomycin C, bleomycin, actinomycin D, irinotecan, 5-fluorouracil, sorafenib, sunitinib, regorafenib, brivanib, orantinib, linsitinib, erlotinib, cabozantinib, foretinib, tivantinib, fotemustine, tauromustine (TCNU), carmustine, cytosine C, cyclophosphonamide, cytosine arabinoside, paclitaxel, docetaxel, methotrexate, everolimus, PEG-arginine deiminase, a tegafur/gimeracil/oteracil combination, muparfostat, peretinoin, gemcitabine, bevacizumab and ramucirumab, floxuridine, GM-CSF, molgramostim, sargramostim, OK-432, interleukin-2, interleukin-4 and TNFalpha, $^{125}$I-labeled anti-CEA (carcinoembryonic antigen) antibodies, microspheres loaded with one of the foregoing, radioelements and complexes of said radioelements with macrocyclic chelates, magnetic particles based on an iron compound and/or on a gadolinium chelate, radioactive microspheres, deoxyribonucleic acid sequences, ribonucleic acid sequences, and combinations thereof.

4. The composition of claim 1, wherein the anthracyclines are chosen from doxorubicin, epirubicin, nemorubicin, and idarubicin.

5. The composition of claim 1, wherein the lipid phase further comprises a non-iodized oil selected from the group consisting of linseed oil, soybean oil, palm oil, coconut oil, castor oil, corn oil, cottonseed oil, peanut oil, sesame oil, sunflower oil, safflower oil, almond oil, olive oil, poppy oil, and an oil comprising or consisting of a mixture of fatty acid triglycerides of formula:

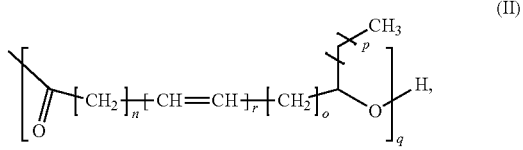

wherein R is an aliphatic chain comprising from 3 to 35 carbon atoms, with the proviso that more than 95% of said fatty acids are C8 and/or O10.

6. The composition as claimed in claim 1, wherein the surfactant has an HLB of 1 to 8.

7. The composition of claim 1, wherein the surfactant is polyglyceryl polyricinoleate or PEG-30 dipolyhydroxystearate.

8. The composition of claim 1, wherein the iodized oil comprises ethyl esters of iodized fatty acids of poppy oil or olive oil.

9. The composition of claim 1, wherein the size of the aqueous phase droplets is from 1 to 200 µm.

10. The composition of claim 1 having a viscosity at 20° C. from 100 to 200 mPa·s and/or a viscosity at 37° C. from 40 to 80 mPa·s.

11. The composition as claimed in claim 1, wherein R₈ represents —CH₂—CH₂OH, —CHOH—CH₂OH, —CH—(CH₂OH)₂, —(CH₂)—(CHOH)ₚ—CH₂OH in which p=1 to 4, or —C—(CH₂OH)₃.

12. A method for preparing a composition as claimed in claim 1, the method comprising:
a) mixing the surfactant in the iodized oil; and
b) mixing the solution obtained in step a) with the aqueous solution comprising the anti-cancer agent and the densifying agent.

13. The composition of claim 1, wherein the densifying agent has the following formula:

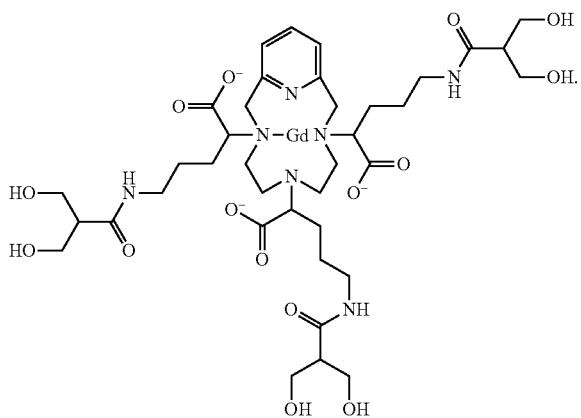

* * * * *